United States Patent [19]

Barnwell

[11] Patent Number: 5,767,066

[45] Date of Patent: Jun. 16, 1998

[54] MEDICAL APPLICATION OF BROMELAIN

[75] Inventor: Stephen George Barnwell, Chester, England

[73] Assignee: Cortecs Limited, Great Britain

[21] Appl. No.: 696,918

[22] PCT Filed: Feb. 21, 1995

[86] PCT No.: PCT/GB95/00352

§ 371 Date: Aug. 19, 1996

§ 102(e) Date: Aug. 19, 1996

[87] PCT Pub. No.: WO95/22348

PCT Pub. Date: Aug. 24, 1995

[30] Foreign Application Priority Data

Feb. 22, 1994 [GB] United Kingdom ............... 9403344

[51] Int. Cl.⁶ ............................................. A61K 38/00
[52] U.S. Cl. ............................................................ 514/2
[58] Field of Search ............................................. 514/2

[56] References Cited

U.S. PATENT DOCUMENTS

| 4,440,749 | 4/1984 | Fugisaki et al. | 424/94 |
| 5,460,812 | 10/1995 | Sipos | 424/94.1 |

FOREIGN PATENT DOCUMENTS

| 0 576 938 A1 | 5/1994 | European Pat. Off. |
| 2121685 | 4/1984 | United Kingdom |

*Primary Examiner*—Kimberly Jordan
*Attorney, Agent, or Firm*—Pennie & Edmonds LLP

[57] ABSTRACT

The application relates to the use of bromelain in the treatment of hypercholesterolaemia and similar diseases. Bromelain is able to act as a bile acid receptor antagonist and therefore to prevent reabsorption of bile acids by the gastrointestinal tract.

5 Claims, No Drawings

MEDICAL APPLICATION OF BROMELAIN

This application is a 371 of PCT/GB95/00352, filed Feb. 21, 1995.

The present invention relates to the use of the mixture of enzymes known as bromelain in the treatment of conditions requiring a reduction or other modification in the bile acid pool. In particular, the invention relates to the treatment and prophylaxis of hyperlipidaemia, especially hypercholesterolaemia.

Coronary heart disease is one of the leading causes of death in the Western World and results from the accumulation of atherosclerotic plaques within the major arteries supplying the heart with oxygen and nutrients. Atherosclerosis progresses for decades without clinical effect gradually constricting the arterial lumen. Coronary Artery Disease is defined as less than 75% occlusion of the arterial lumen, Coronary Heart Disease is defined as greater than 75% occlusion. Symptoms occur when a vessel becomes completely blocked; angina (sharp chest pain) or myocardial infarction (heart attack), or sometimes sudden death. A number of major risk factors have been identified for Coronary Artery and Coronary Heart Disease: age, male sex, hypertension, cigarette smoking, lack of exercise, stress, diet, diabetes, lifestyle and elevated serum cholesterol (hypercholesterolaemia; particularly where the cholesterol is carried as LDL-cholesterol).

Cholesterol is an important component of cell membranes, steroid hormones and bile acids. Approximately two thirds of the daily cholesterol requirement is met by endogenous synthesis by the liver, the remainder being supplied by the diet. Cholesterol is an insoluble lipophilic material which requires encapsulation in lipoproteins before it can be transported in the blood. The main types of lipoproteins are chylomicrons, very low density lipoprotein (VLDL), intermediate-density lipoprotein (IDL), low density lipoprotein (LDL) and high density lipoprotein (HDL). The liver secretes cholesterol into the blood as VLDL that is converted into IDL, which is in turn converted into LDL. LDL makes up about two thirds of the cholesterol carried in the blood where it is transported back to the liver with the help of HDL. Many cells exhibit LDL receptors on their surface enabling the uptake and extraction of LDL cholesterol for synthesis of cellular components. It is the liver, however, which is responsible for the extraction of most LDL-cholesterol, where it may be secreted into the blood or alternatively into bile (either as bile acids or free cholesterol). Chylomicrons are made by gastrointestinal cells from lipids, including cholesterol, absorbed from the diet, secreted into the lymph and subsequently enter the systemic blood supply where peripheral tissues break down and utilise the lipid components. The resulting chylomicron remnants are returned to the liver.

Elevated blood LDL levels may be reduced in a number of ways with a concomitant decrease in the risk of developing disorders associated with atherosclerosis. Normal serum cholesterol levels are defined as below 200 mg/dl, mild hypercholesterolaemia requiring modification to the diet as 200–220 mg/dl, moderate hypercholesterolaemia as 220–260 mg/dl and severe hypercholesterolaemia, requiring drug and dietary intervention, as more than 260 mg/dl. T. Gordon, W P Castelli, M C Hjortland, W B Kannel and T R Dawber (1984), *Predicting Coronary Heart Disease in Middle-Aged and Older Persons*. The Framingham Study: *Journal of the American Medical Association* (1977); 238, 497. National Institute of Health Consensus Development Conference Statement on Lowering Blood Cholesterol, Dec. 10–12th (1984).

When hypercholesterolaemia is detected, a series of possible treatments may be considered:

(i) Diet

For mild and moderate hypercholesterolaemia the initial recommended therapy is not drugs but diet. Dietary modification includes a reduced consumption of foods rich in cholesterol and saturated fat such as eggs, dairy products and red meat.

(ii) Drugs

In patients with severe hypercholesterolaemia or moderate hypercholesterolaemia which is resistant to changes in diet then drug treatment may be considered. These include:

Cholestyramine is a bile acid sequestrant, or binding agent, that interrupts the recycling of cholesterol, in the form of bile acids, back to the liver. Bile acids, which are synthesised from cholesterol by the liver, are usually actively conserved in the enterohepatic circulation. Cholestyramine, following oral administration, binds to bile acids in the duodenum forming an insoluble complex which is subsequently excreted from the body in the faeces. Interruption of the enterohepatic circulation results in the upregulation of bile acid synthesis from cholesterol in the liver. This increased requirement for cholesterol is sourced partly from newly synthesised hepatic cholesterol, the remainder via increased uptake of LDL-cholesterol from the blood. Enhanced hepatic uptake of LDL-cholesterol results in an overall lowering in blood-cholesterol concentrations.

Patients receiving cholestyramine typically experience a 13% decrease in serum-cholesterol, a 20% reduction of LDL-cholesterol, and a 24% reduction in deaths associated with Coronary Heart Disease. Effective cholestyramine treatment has a number of drawbacks related to its unpalatable administration; presenting as unit-dose packets containing 4 g of granules which are mixed with water or fruit juice. Up to 9 unit-dose packs (average 3–6) in single or divided doses may be required daily for prolonged periods, which results in poor patient compliance (typically 30% stop taking the medication). Cholestyramine granules have the appearance of small plastic beads and are reported to have the texture of liquified sandpaper. A high incidence of gastrointestinal discomfort is associated with Cholestyramine treatment, there is also an increased risk of bleeding on long term therapy and a number of important drug interactions with digitalis, antibiotics and diuretics. Dietary supplements of vitamins A, D and K are required on long term treatment. Cholestyramine is also expensive to manufacture, which is reflected in its high treatment cost.

HMGCoA-reductase inhibitors

Examples of HMGCOA reductase inhibitors include pravastatin and simvastatin. These drugs act by inhibiting the endogenous synthesis of cholesterol, mainly in the liver, by competitively inhibiting the rate limiting enzyme in cholesterol biosynthesis. Large reductions in plasma cholesterol levels of up to 40% may be achieved with this type of therapy.

Restricting the supply of endogenously synthesised cholesterol means that the liver can only obtain cholesterol for the manufacture of cellular components, secretions and bile acids from the blood. This results in a massive upregulation in LDL-receptor activity causing a subsequent reduction in serum cholesterol and LDL-cholesterol levels. Reductions in serum LDL-cholesterol levels are associated with an increase in 'protective' serum HDL-cholesterol levels. The most common side-effect from HMGCoA reductase inhibitors is gastrointestinal distress, others include fatigue, rash, elevated hepatic transminase levels and headache. More recently, large detailed studies have questioned the long term effectiveness of HMGCoA reductase inhibitors in reducing death rates. Statistical analysis has shown that any benefit is overshadowed by an unexplained increase in the incidence of violent death (murder, suicide and accidents).

Other Drug Treatments

Other examples of drugs used to treat hypercholesterolaemia include the isobutyric acid derivative and nicotinic acid derivatives.

Isobutyric acid derivatives include bezafibrate, clofibrate, fenofibrate and gemfibrozil. These drugs effectively reduce plasma triglycerides and VLDL, raise HDL, and can reduce LDL-cholesterol by up to 18%. Isobutyric acid derivatives cause about a 10% incidence of side-effects (which are mainly gastrointestinal or central nervous system). Animal studies have shown tumours and gallstone formation with these compounds.

Nicotinic acid derivatives lower both triglyceride and serum cholesterol levels. They inhibit lipolysis in adipose tissues, decrease esterification of triglycerides in the liver and increase the activity of lipoprotein lipase. The resultant fall in VLDL levels is followed by a decrease in IDL and LDL, which may be up to 20%, and an increase in HDL levels. Nicotinic acid produces intense flushing and headache which may be reduced by slowly titrating the dose. Gastrointestinal disturbances are also common with this medication.

The potential for unpleasant side-effects, high cost, or questionable efficacy of existing treatments for hypercholesterolaemia ensures that there is still a considerable opportunity for improvements in this therapeutic area. Ideally the treatment should have few, if any, side effects, low toxicity risk and, because of the extended periods necessary to control this condition, the treatment should be convenient and well tolerated e.g. (once-a-day, once-a-week). The cost of the treatment should also be low.

The present invention relates to the control of hypercholesterolaemia and other conditions mediated by bile acids by a modification of the bile acid pool.

Bile acids (or bile salts—the exact nature and proportion of the species present will depend on the pH of the environment and so the terms are used interchangeably) are a group of naturally occurring detergents which form a major component of bile. As briefly mentioned above, bile acids are synthesised in the liver from cholesterol by hydroxylation and other modifications and represent the end product(s) of cholesterol metabolism. In its role as an exocrine gland the liver secretes bile; the secretion of bile acids providing the osmotic driving force for a major proportion of bile flow. In some species, bile undergoes storage and concentration in the gallbladder until food is consumed, whereupon gallbladder contraction and emptying takes place in response to the gastrointestinal hormone cholescystokinin. Bile acids subsequently enter the duodenum where they perform their major role as surfactants; enhancing the digestion and absorption of dietary lipids and lipid soluble vitamins. Bile acids also increase the action of pancreatic lipases.

After completing their role in digestion, bile acids are avidly conserved by the body: they are efficiently reabsorbed by an active receptor mediated process from the terminal ileum and returned to the liver, via the hepatic portal vein, and undergo further receptor enhanced extraction prior to resecretion into the bile.

The almost continuous flow of bile acids is topographically localised and limited to the liver, biliary tree, intestine, enterocytes and hepatic portal venous system, and thus comprises the enterohepatic circulation. The enterohepatic circulation functions not only to conserve valuable detergent bile acid molecules, by allowing their many times repeated use, but also allows bile acids to maintain continuous homeostatic control over a variety of metabolic events. Bile acids have an essential role in regulating the synthesis and transport of a variety of lipids within and between cells, tissues and organs which encounter the bile acids during their enterohepatic circulation.

The human bile acid pool contains approximately 3 g of bile acids which are typically recycled 4–12 times daily. Faecal excretion accounts for 0.2 to 0.6 g daily, this amount being made up by synthesis from cholesterol in the liver. The efficient reabsorption of bile acids from the digestive tract is the result of both active and passive transport mechanisms; more than 95% of bile acids are removed by these processes.

The active transport system resides in the terminal ileum and bears a number of similarities to the hepatic active transporter which removes bile acids from the hepatic portal blood supply. The ileal bile acid transporter demonstrates saturation kinetics, competitive inhibition and dependency on the presence of sodium ions. The sodium gradient necessary to drive bile acid uptake is thought to be provided by the $Na^+/K^+$-ATPase present on the basolateral membrane of ileocytes. Bile acid uptake involves an apical membrane bile acid/$Na^+$ cotransporter and a bile acid-anion exchange system in the basolateral membrane. Evidence would suggest that the bile acid absorption occurs via a protein, molecular weight 99 kDa, found in the ileum but absent from the jejunum with a specific bile acid binding site.

Alternatively bile acid absorption across the small intestine and colon may occur by ionic and nonionic diffusion. Although it seems that, in reality, only nonionic diffusion makes up a significant (90%) proportion of the total.

The main determinant of the absorption pathway of a bile acid is its relative hydrophilicity:hydrophobicity which is determined by the structure. In general, the more hydrophobic bile acids such as deoxycholic and chenodeoxycholic acid have an increased tendency to be absorbed via passive diffusion while more hydrophilic bile acids such as cholic acid are more likely to be absorbed via the active transporter. In vivo, most bile acids are amidated with either glycine or taurine and this has the effect of lowering their pKa (dissociation constant) and thus increasing their tendency to ionize at gastrointestinal pH, therefore necessitating their absorption through the active bile acid transporter.

As mentioned above, it is likely that the ileal bile acid transporter is a transmembrane protein with the bile acid binding site protruding into the gastrointestinal lumen. It may be therefore envisaged that an agent which interacts with or inactivates the lumenal part of the receptor would prevent bile acid transport taking place. An example of an agent which could inhibit the bile acid receptor is a chemically modified bile acid which irreversibly combines with the bile acid receptor binding site or an agent which removes the bile acid binding sites from the surface of the gastrointestinal cells (see, e.g. Wess et al, *J. Med. Chem.*, 37: 873–875 (1994)). Inactivation of the ileal bile acid receptor would likely result in an increased loss of bile acids in the faeces, an increase in hepatic bile acid synthesis and concomitant upregulation of hepatic LDL receptor activity. Upregulation of hepatic-LDL receptor activity would have the beneficial effect of reducing serum LDL-cholesterol levels.

Therefore, an agent capable of increasing hepatic-LDL receptor activity would be of use in the treatment of hypercholesterolaemic patients, particularly those affected by the side effects of other treatments.

We have now made the surprising discovery that bromelain is capable of decreasing the efficiency of bile acid reabsorption by the gastrointestinal tract.

Therefore, in a first aspect of the present invention, there is provided the use of bromelain in the preparation of an agent for reducing or preventing bile acid reabsorption by the gastrointestinal tract.

As a result of its effect on the reabsorption of bile acids by the gastrointestinal tract, bromelain will be of benefit to patients suffering from hyperlipidaemia, particularly hypercholesterolaemia. In addition, bromelain is capable of reducing the enterohepatic circulation of bile acids and therefore of benefitting patients suffering from cholestatic liver disease or hepatic insufficiency. In these conditions, the recycling of a normal bile acid pool through an impaired liver can further damage remaining hepatic function.

The invention will also be useful in a method for the treatment of a patient suffering from a condition mediated by the size of the bile acid pool, the method comprising administering to a patient suffering from such a condition an effective amount of bromelain.

It is believed that the mechanism of action of bromelain in the present invention is to antagonise the ileal bile acid receptors although the effectiveness of the enzymes in the present invention is not affected by the accuracy of this theory. This mechanism of action also does not require that bromelain is absorbed intact from the gastrointestinal tract.

Bromelain is the collective name for the proteolytic enzyme composition found in the tissues of the plant Bromeliaceae. Bromelain is a mixture of various moieties derived from the stem of the pineapple (*Ananas comosus*). It contains at least two proteolytic enzymes but also non-proteolytic enzymes, including an acid phosphatase and a peroxidase; it may also contain amylase and cellulase activity. In addition, various other components are present, in particular, organically bound calcium. The known proteolytic enzymes of bromelain and papain share a high degree of amino acid sequence homology around the active centre, and evidence suggests that bromelain and papain use the same catalytic mechanism. Bromelain differs from papain, however, in having a different specificity of cleavage. In addition, the known proteolytic enzymes of bromelain are glycoproteins, whereas papain is a simple protein. Bromelain is reviewed by Taussig and Batkin (*J. Ethnopharmacol.* 22 191–203 (1988)).

As early as the fifteenth century, bromelain has been used as a digestive aid, as a cleansing agent to improve the texture of skin, and to treat wounds to promote healing. Recently, a vast accumulation of knowledge on its pharmacological and biological effects have resulted in bromelain being available for clinical use in man. In particular, bromelain is used as an adjunct in the treatment of soft tissue inflammation and oedema associated with trauma and surgery. Bromelain is available in various countries under the trademarks ANANASE FORTE, ANANASE, EXTRANASE, PROTEOLIS, RESOLVIT, ROGORIN, BROMASE and TRAUMANASE. In clinical use over a period of more than 30 years, there have been few reports of significant undesirable effects.

Documents which discuss other medical applications of bromelain include International patent application No. PCT/GB93/01374 which describes the use of proteolytic enzymes including bromelain in the treatment of diarrhoea in humans. However there is no reference in the application to the treatment of conditions other than diarrhoea and certainly no reference to the blocking of bile acid reabsorption by the gastrointestinal tract or to the decrease of blood lipid levels.

UK patent application No. 9313188 relates to the use of a single component of the bromelain mixture. The document discusses the use of stem bromelain in the mediation of cyclic nucleotide pathways. However, it does not suggest that either stem bromelain or, indeed, any other component of bromelain could be useful in preventing the reabsorption of bile acids.

Although any route of administration may be used, the bromelain will generally be administered orally since it is intended to operate in the gastrointestinal tract. It may be administered in the form of tablets, syrups, elixirs or hard or soft gelatin capsules, which may be enteric coated.

The preferred delivery system for the bromelain in the present invention would be controlled release to ensure at least partial removal of bile acid receptors from the enterocytes situated in the terminal ileum. It would be desirable to have a combination of gastric protection (to prevent degradation of the bromelain in the stomach), and a delay in release of the bromelain protease until the terminal ileum. Delayed release of bromelain would help to ensure that other receptors present in the small intestine used for the digestion and absorption of nutrients remain intact.

The delayed release of the bromelain may be achieved by a number of formulation strategies, singly or in combination.

Another formulation strategy which may be employed is to formulate the bromelain with a thermosoftening solid (at physiological temperatures). Rapid or sustained release delivery of bromelain may be achieved by administering with one or more polyglycolysed glycerides or other suitable and physiologically compatible compounds having a phase transition temperature (melting point) above 37° C. Suitable glycerides include di- and tri-glycerides, such as many of the GELUCIRE compounds, which are hydrogenated fatty acid esters available from Gattefosse. (The word GELUCIRE is a trademark). Other trademarks of suitable glycerides include LABRAFIL and PRECIROL. Care should be taken to choose formulation systems which do not require heating to an extent which will cause the thermal decomposition of the enzyme: in general, the temperature should be kept below about 60° C. Specific examples of exemplary GELUCIRE compounds, and their equivalents include:

GELUCIRE 50/02;

GELUCIRE 46/07;

GELUCIRE 48/09;

GELUCIRE 50/13; and

GELUCIRE 53/10.

The first two digits in the numeric portion of the GELUCIRE name represent the liquid/solid phase transition temperature in degrees centigrade and the second two digits represent the hydrophile/lipophile balance (HLB) value. The type of GELUCIRE used (or blend of GELUCIRES) should be selected to give the appropriate desired release characteristics, which may be rapid or sustained release or a combination of release profiles.

Various formulation aids may be present. For example, a surfactant, such as one or more of those discussed below in more detail, may be included in rapid or sustained release formulations. Surfactants may be used to modify the release characteristics of bromelain from a formulation, particularly one containing glycerides. Another formulation aid which may be present is a fluidiser and/or thickening agent such as colloidal silicon dioxide; for example the preparation available under the trade mark AEROSIL (for example AEROSIL 200). Colloidal silicon dioxide may also be used to modify the release rate of bromelain from formulations based on thermosoftening agents such as GELUCIRES.

A further approach to formulating the component(s) for sustained release is to use a thixotropic material. Such materials behave as fluids when stressed by shearing forces (such as may be induced by stirring or pumping) but become non-flowing gels when the shearing force is removed. Like thermosoftening vehicles, described above, thixotropic vehicles are well suited to hard gelatin encapsulation technology. Suitable thixotropic vehicles include colloidal silicon dioxide (such as the AEROSIL 200 preparation previously referred to) and ethyl cellulose. Other components which may be present include gel promoters and dispersion aids. Glycols such as polyethylene glycol (for example PEG 400) are useful gel promoters in thixotropic formulations and also assist dispersion. Non-ionic surfactants, such as polyethoxylated, optionally hydrogenated, castor oil, for example having HLB values in the range 12 to 14 or 14 to 16, may be used. The gel composition may be varied within quite wide limits while acceptable performance. It may also be an advantage to formulate part of the active ingredients for sustained release and part for non sustained release. This may be achieved by incorporating part of the enzyme in a matrix containing sustained release GELUCIRES described above and part of the enzyme in more rapidly dispersible GELUCIRES such as:

GELUCIRE 35/10;
GELUCIRE 33/01;
GELUCIRE 37/02; and
GELUCIRE 44/14.

GELUCIRE 44/14 is particularly useful because of its solubility in water. These materials may be filled into hard or soft gelatin capsules.

It is not necessary for any other ingredient to be present. However, in some cases suitable antioxidants may be added and these included d-alpha-tocopherol, dl-alpha-tocopherol, butylated hydroxytoluene (BHT) and butylated hydroxyanisole (BHA). Antioxidants can be used either singly or in combination. Another optional ingredient is a surfactant, as briefly mentioned above. Suitable surfactants are either ionic or nonionic, but in general do not include bile acids or their salts. Nonionic surfactants are preferred. A suitable HLB range for the surfactant, if present, is broadly from 0 to 20, preferably from 6 to 18 and typically from 10 to 18. Examples of suitable surfactants, which may be used singly or in combination, include the polyoxyethylene sorbitan fatty esters (eg polysorbate 80, polysorbate 60, polysorbate 40, polysorbate 20), the poloxyethylene stearates (eg polyoxyl-40-stearate) and the polyoxyethylene, optionally hydrogenated, castor oil derivatives such as the CREMOPHOR RH40 and EL products. The word CREMOPHOR is a trade mark. It is generally preferred that pharmaceutical formulations in accordance with the invention be substantially non-aqueous, in the sense that no water is added. Some water may be present in the ingredients used. However, water-free formulations need not be preferred for all applications.

Formulations in accordance with the invention may be enteric coated or otherwise protected to ensure better survival of the pharmaceutically active compound through the stomach. Any convenient enteric protection method may be used. Capsules containing the formulation may be coated with an enteric coat such as hydroxypropyl methylcellulose phthalate or by the commercial coating process of Pharma-Vinci A/S, based on the use of methacrylic acid copolymer in a suitable solvent.

The dosage of bromelain will depend on the individual needs of the patient being treated. Dosage of bromelain is conventionally measured in BTU (bromelain tyrosine units), CDU (casein digestion units), GDU (gelatin digestion units) or MCU (milk clotting units). BTUs, CDUs and GDUs are as defined in the literature, as follows:

BTU

One bromelain tyrosine unit is that amount of enzyme which will liberate one micromole of tyrosine per minute under the conditions of the assay (for example, after digestion of an acid denatured haemoglobin substrate at pH 5 and 30° C).

CDU

That amount of enzyme which will liberate one microgram of tyrosine after one minute digestion at 37° C. from a standard casein substrate at pH 7.0.

GDU

The enzyme activity which liberates one milligram ($10^{-3}$ g) of amino nitrogen from a standard gelatin solution after 20 minutes digestion at 45° C. and at pH 4.5.

1100 BTU/g=750 CDU/mg=1200 GDU/g.

While the precise dosage will be under the control of the physician, daily dosages of from 50 to 4000 GDU/day and preferably from 100 to 1000 GDU/day may be appropriate. The daily dose may be given in one or more aliquots per day, for example once, twice, three or four times a day. Alternatively, treatment may only be required once or twice weekly for certain conditions.

The invention will now be illustrated by the following examples.

EXAMPLE 1

The formulation used is an example of a thermosoftening vehicle. Typically these materials melt upon heating, thereby allowing the use of conventional mixing and pumping technology for fluid filling.

Material Quantity

Capsule potency 275 GDU/capsule

|  | mg/capsule | w/w (%) |
|---|---|---|
| Bromelain | 90.00 mg | 27.3 |
| GELUCIRE 35/10 | 225.0 mg | 68.2 |
| AEROSIL 200 | 15.0 mg | 4.5 |
|  | 330.0 mg | 100.0 |

The Gelucire 35/10 was melted by heating to around 40° C. Bromelain and AEROSIL 200 were added until completely dispersed. A total of 330 mg of the formulation was filled into size "1" hard gelatin capsules while hot and then allowed to solidify with cooling. Capsules may subsequently be sealed by gelatin banding.

Enteric Coating

To prevent premature release of bromelain from the delayed release formulation described above an enteric-coat may be applied to the hard gelatin capsule, for example using the commercial process of Pharma Vinci A/S (Denmark). The enteric coating is applied to the capsules in aqueous ethanolic solution by spray-coating in a Combicoata.

EXAMPLE 2

Effect of Bromelain on Faecal Excretion of Bile Acids.

Two formulations of bromelain were prepared for testing in healthy human volunteers. The formulations were as follows:

A: one size 1 hard gelatin capsule containing 276 gelatin digestion units of bromelain;

B: one size 0 hard gelatin capsule containing 1104 gelatin digestion units of bromelain.

The hard gelatin capsules were enteric coated and therefore designed to release a bolus of bromelain after leaving the acidic environment of the stomach.

The study was conducted over a 5-day period. An initial 2-day treatment-free period was followed by a three day post-dose surveillance interval. The medication was administered after an overnight fast with 250 ml of water. Food was allowed 3 hours post-dose.

Faecal samples for each 24-hour period were pooled, weighed and homogenised in a sterile blender. An approximately 50 g sample of the homogenate was then taken and frozen at −70° C. until analysed.

Analysis of the faecal samples was carried out by the following method.

1. After thawing, faecal samples were freeze-dried overnight and the samples ground to a fine-homogenous mixture.

2. Soxhlet extractions were carried out overnight (approx. 16 h) on 500 mg of freeze-dried faeces with 50 ml of 50% (v/v) chloroform:methanol.

3. An aliquot (10 ml) of this extract was evaporated to dryness at 50° C. under a stream of air and redissolved in 500 µl of methanol for bile acid determination.

4. The bile acid content of the samples was determined by a specific enzyme assay based on 3 α hydroxy-steroid dehydrogenase described by Coleman et al, *Biochem. J.*, 178, 201–208 (1979).

Results

The medication was well tolerated in all cases with no side-effects reported.

TABLE 1

Effect of bromelain on the faecal excretion of bile acids.

| SUBJECT | Pre-dose | Post-dose | Ratio Post-dose/Pre-dose |
|---|---|---|---|
| Dose: 276 GDU of bromelain | | | |
| 1 | 512 | 788 | 1.54 |
| 2 | 101 | 199 | 1.97 |
| 3 | 227 | 396 | 1.74 |
| mean (± sem) | 280 (±122) | 461 (±266) | 1.65 |
| Dose: 1104 GDU of bromelain | | | |
| 4 | 51 | 281 | 5.51 |
| 5 | 31 | 148 | 4.47 |
| 6 | 121 | 212 | 1.75 |
| mean (± sem) | 68 (±27) | 214 (±38) | 3.15 |

The values represent the mean daily faecal loss of bile acids in mg/day in the pre- and post-dose periods.

The mean daily bile acid output in the pre- and post-does periods was calculated and is shown in Table 1. An increase in the mean faecal bile acid output was observed after administration of bromelain of 165% and 315% for the 276 GDU and 1104 GDU dose respectively. A further observation was the stool colour change post-dose, reflecting the distinctive red-brown colour of bromelain. This observation correlates well with observed increases in faecal bile acid output.

Conclusions

The increased faecal excretion of bile acids observed in volunteers after receiving bromelain suggests that, under suitable conditions, the gastrointestinal bile acid receptor may be inactivated by proteolytic degradation.

EXAMPLE 3

Effects of Bromelain on Plasma Cholesterol and Triglyceride Levels in Healthy Volunteers.

Following the observation that bromelain increases the faecal excretion of bile acids, detailed in Example 2, a further study was carried out to investigate whether this phenomenon translated into a reduction in plasma cholesterol levels, important in reducing the risk of developing Coronary Artery Disease. Twenty-one healthy male volunteers received either a placebo or an enteric-coated bromelain formulation, containing approximately 500 gelatin digestion units of the enzyme, for 10 consecutive days. Plasma cholesterol and triglyceride levels were determined by standard hospital, laboratory test methods before initiating treatment and at the end of the study period.

Results

The results of this study show that ten days' bromelain treatment reduced plasma cholesterol levels by an average of 17%, and plasma triglyceride levels by 31%. Reductions observed in the control groups during this period were less than 10% in the case of both plasma cholesterol and triglyceride (see Table 2 below)

TABLE 2

Effect of bromelain treatment on plasma triglyceride and cholesterol levels.

| Bromelain Treated Group | | Placebo Treated Group | |
|---|---|---|---|
| Pre-Treatment Triglyceride (mg/l) n = 10 | Post-Treatment Triglyceride (mg/l) n = 10 | Pre-Treatment Triglyceride (mg/l) n = 11 | Post-Treatment Triglyceride (mg/l) n = 11 |
| 270 ±80 | 185 ±38 | 120 ±17 | 110 ±15 |
| Pre-Treatment Cholesterol (mg/l) n = 10 | Post-Treatment Cholesterol (mg/l) n = 10 | Pre-Treatment Cholesterol (mg/l) n = 11 | Post-Treatment Cholesterol (mg/l) n = 11 |
| 189 ±9 | 156 ±7 | 166 ±9 | 151 ±6 |

Values are means ±sem of 10 or 11 observations.

Conclusions

Treatment of healthy volunteers for 10 days with an enteric-coated bromelain product reduces the levels of plasma triglyceride and cholesterol, which are important risk factors in the development of Coronary Artery Disease.

I claim:

1. A method for reducing or preventing bile acid reabsorption by the gastrointestinal tract, the method comprising administering to a patient an effective amount of bromelain.

2. A method for the treatment or prophylaxis of cholestatic liver disease or hepatic insufficiency, the method comprising administering to a patient an effective amount of a composition in which the sole active component is bromelain.

3. The method as claimed in claim 1 or 2, wherein the bromelain is formulated for oral delivery.

4. The method as claimed in claim 1 or 2, wherein the bromelain is in a delayed release formulation.

5. The method as claimed in claim 1 or 2, wherein the bromelain is enterically protected.

* * * * *